US011850107B2

(12) United States Patent
Jensrud et al.

(10) Patent No.: US 11,850,107 B2
(45) Date of Patent: Dec. 26, 2023

(54) CUTTING TOOL CLEANING ACCESSORY

(71) Applicant: Boston Scientific Scimed, Inc., Maple Grove, MN (US)

(72) Inventors: Allyn N. Jensrud, Milford, MA (US); Todd M. Pfizenmaier, Sturbridge, MA (US); Kathleen M. Laliberte, Littleton, MA (US); Rachael Campion, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/059,128

(22) Filed: Nov. 28, 2022

(65) Prior Publication Data
US 2023/0103741 A1 Apr. 6, 2023

Related U.S. Application Data

(63) Continuation of application No. 16/834,003, filed on Mar. 30, 2020, now Pat. No. 11,534,262.

(60) Provisional application No. 62/832,746, filed on Apr. 11, 2019.

(51) Int. Cl.
*A61B 90/70* (2016.01)
*B08B 9/02* (2006.01)
*B08B 9/04* (2006.01)

(52) U.S. Cl.
CPC .............. *A61B 90/70* (2016.02); *B08B 9/021* (2013.01); *B08B 9/04* (2013.01); *A61B 2090/701* (2016.02); *B08B 2209/04* (2013.01)

(58) Field of Classification Search
CPC ... A61B 90/70; A61B 2090/701; B08B 9/021; B08B 9/04; B08B 2209/04

USPC .................................................. 15/21.2, 160
See application file for complete search history.

(56) References Cited

U.S. PATENT DOCUMENTS

| 3,583,016 | A | * | 6/1971 | McConnell | A63B 47/04 |
| | | | | | 15/21.2 |
| 5,647,082 | A | * | 7/1997 | Garske | A63B 47/04 |
| | | | | | 15/21.2 |
| 2006/0264988 | A1 | | 11/2006 | Boyle | |
| 2007/0180636 | A1* | | 8/2007 | Rosquist | A63B 47/04 |
| | | | | | 15/21.2 |
| 2009/0242001 | A1 | | 10/2009 | Efinger et al. | |
| 2016/0166135 | A1 | | 6/2016 | Fiset | |

(Continued)

FOREIGN PATENT DOCUMENTS

WO 2017074984 A1 5/2017

OTHER PUBLICATIONS

International Search Report and Written Opinion issued in International Application No. PCT/US2020/025678, dated Jul. 10, 2020 (12 pages).

*Primary Examiner* — Randall E Chin
(74) *Attorney, Agent, or Firm* — Bookoff McAndrews, PLLC

(57) ABSTRACT

The present disclosure relates generally to the field of medical devices and medical device accessories. In particular, the present disclosure relates to a tool or accessory for cleaning a medical device. For example, the tool or accessory may clean a fluid delivery lumen of an endoscopic submucosal dissection (ESD) knife. The tool or accessory may include a housing with a first portion of an elongate member secured within a first portion of the housing and a second portion of the elongate member extending into a chamber of the housing.

20 Claims, 8 Drawing Sheets

(56) References Cited

U.S. PATENT DOCUMENTS

| | | |
|---|---|---|
| 2017/0106128 A1 | 4/2017 | Bagwell et al. |
| 2017/0172700 A1 | 6/2017 | Denzinger et al. |
| 2019/0231183 A1 | 8/2019 | Ahmed et al. |

* cited by examiner

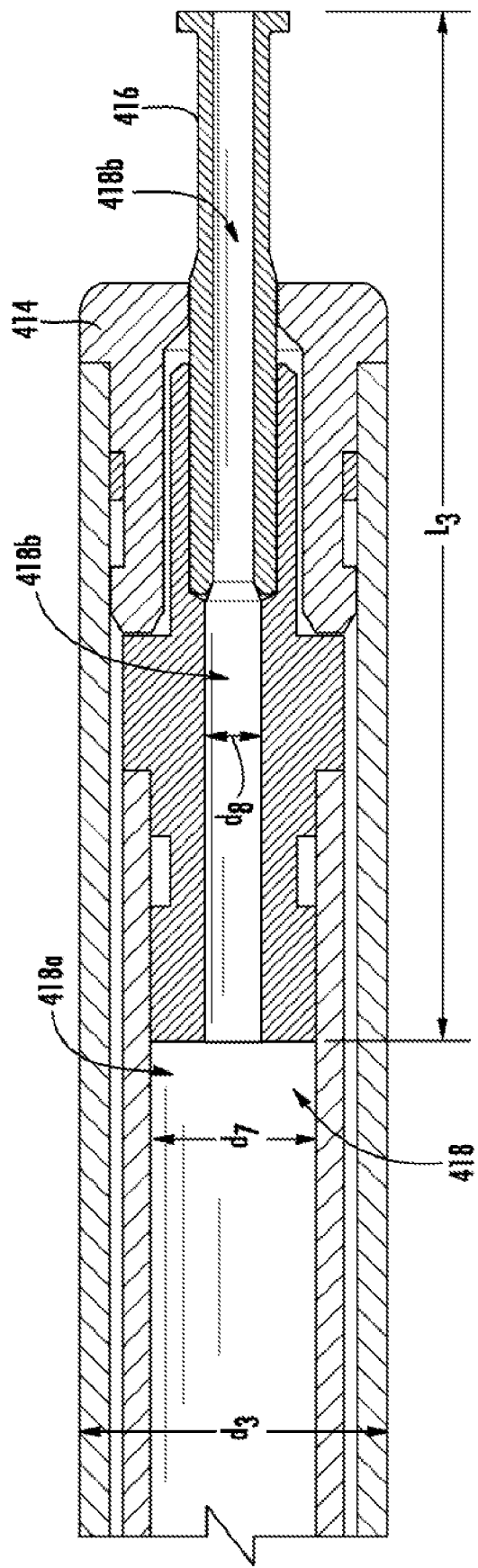

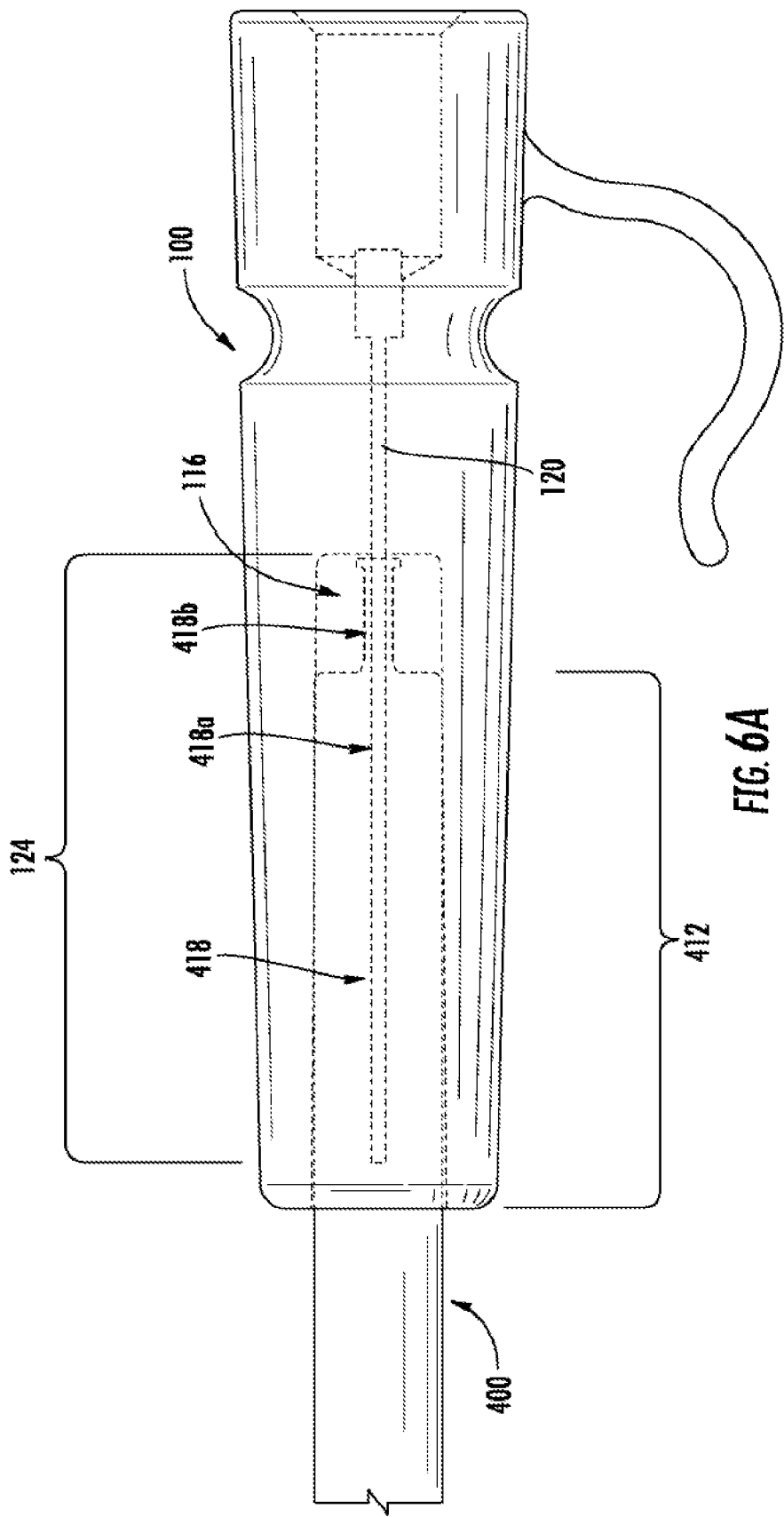

CUTTING TOOL CLEANING ACCESSORY

CROSS-REFERENCE TO RELATED APPLICATIONS

This application is a continuation of U.S. patent application Ser. No. 16/834,003, filed on Mar. 30, 2020, now U.S. Pat. No. 11,534,262, which claims priority to U.S. Provisional Patent Application No. 62/832,746, filed on Apr. 11, 2019, the disclosure of each of which is incorporated herewith by reference.

FIELD

The present disclosure relates generally to the field of medical devices and medical device accessories. In particular, the present disclosure relates to a tool or accessory for cleaning a medical device.

BACKGROUND

Certain devices have a fluid delivery lumen that may benefit in performance from cleaning. For example, endoscopic submucosal dissection (ESD) knives with injection capability are designed to inject fluid into the submucosal plane to raise a target lesion and provide a safety cushion while the target lesion is dissected. An ESD knife with the combined capabilities of tissue dissection and fluid injection reduces overall procedure time and minimizes the costs associated with performing these steps using separate medical instruments. A drawback of ESD knives with fluid injection capability is the tendency of the fluid delivery lumen to become blocked or otherwise obstructed by accumulated cellular debris, especially during longer endoscopic procedures. The inability to provide/maintain adequate fluid injection throughout the entirety of an endoscopic procedure may result in poor patient outcomes, increased procedure times and/or the need to use multiple ESD knives for a single procedure.

A variety of advantageous medical outcomes may therefore be realized by the medical device cleaning tools or accessories, and method of use, of the present disclosure.

SUMMARY

In one aspect, the present disclosure relates to a medical device cleaning tool comprising a housing, a chamber and an elongate member. The housing may include a first portion and a second portion. The chamber may be formed within the second portion of the housing. The chamber may define an opening at a distal end of the housing. The elongate member may be disposed within the housing. A first portion of the elongate member may be secured within the first portion of the housing and a second portion of the elongate member may extend into the chamber.

In the described and other embodiments, an inner dimension of the chamber may be substantially constant along a full length of the chamber. The second portion of the elongate member may be substantially centered within the chamber. The second portion of the elongate member may include a substantially cylindrical outer dimension. The second portion of the elongate member may include a helical groove. The helical groove may extend along a full length of the second portion of the elongate member. The second portion of the elongate member may include a helical twist. The helical twist may extend along a full length of the second portion of the elongate member. The opening and chamber of the housing may include an inner dimension configured to receive a corresponding outer dimension of a medical device. The first portion of the elongate member may include an anchoring element configured to secure the elongate member within the housing. The anchoring element may include a flattened or deformed portion of the elongate member. The anchoring element may include an enlarged end section attached to a proximal end of the elongate member. The housing may include a decreasing diameter taper from the first to second portions of the housing. A clip attachment may be disposed on an outer surface of the first portion of the housing. One or more surface features may be formed on or within an outer surface of the first portion of the housing. The second portion of the elongate member may include an outer dimension configured to extend into a fluid delivery lumen of the medical device. The fluid delivery lumen may include an injection lumen and a main lumen. The second portion of the elongate member may include a length sufficient to extend through the injection lumen and into the main lumen. The injection lumen may include an inner dimension less than an inner dimension of the main lumen and greater than an outer dimension of the second portion of the elongate member.

In another aspect, the present disclosure relates to a medical device cleaning tool comprising a housing, a chamber, an elongate member, a plate and a spring. The housing may include a first portion and a second portion. The chamber may be formed within the second portion of the housing. The chamber may define an opening at a distal end of the housing. The elongate member may be disposed within the housing. A first portion of the elongate member may be secured within the first portion of the housing and a second portion of the elongate member may extend into the chamber. The plate may be disposed within the chamber. The plate may define an opening configured to receive the second portion of the elongate member. The spring may be disposed within the chamber and around the elongate member proximal to the plate.

In the described and other embodiments, the opening of the chamber may include an inner dimension less than an inner dimension of the remaining portion of the chamber. The inner dimension of the opening may define a first planar surface configured to contact a distal end of the spring and a proximal end of the chamber may define second planar surface configured to contact a proximal end of the spring. The plate may be configured to move from a first axial position in which the plate is in contact with the first planar surface and the spring is non-compressed between the first and second planar surfaces and a second axial position in which the plate is not in contact with the first planar surface and the spring is compressed between the first and second planar surfaces. The plate may be configured to support the elongate member as the plate moves within the chamber. The plate may be configured to move from the first to second axial positions when a distal portion of a medical device is advanced into the chamber. The plate may be configured to move from the second to first axial positions when a distal portion of a medical device is removed from within the chamber.

In yet another aspect, the present disclosure relates to a medical device cleaning tool comprising a housing, a chamber, an elongate member, a plate, a plunger, a surface feature and a spring. The housing may include a first portion and a second portion. The chamber may be formed within the second portion of the housing. The chamber may define an opening at a distal end of the housing. The elongate member may be slidably disposed within the housing. The plate may be attached to a proximal end of the elongate member. The plunger may be attached to the plate. A portion of the plunger may extend through a portion of a wall of the housing at a proximal end of the housing. The surface feature may include a first planar surface and a second planar surface extending into a proximal portion of the housing. The surface feature may define an opening configured to slidably receive the elongate member. A spring may be disposed around a first portion of the elongate member and between the second planar surface of the surface feature and a third planar surface of the plate.

In the described and other embodiments, the plunger may be configured to move from a first position with the spring substantially relaxed between the second and third planar surfaces and a second position with the spring compressed between the second and third planar surfaces. The second portion of the elongate member may not extend distally beyond the opening of the surface feature when the plunger is in the first position. The second portion of the elongate member may extend distally beyond the opening of the surface feature when the plunger is in the second position.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 5A-5B provide perspective views of an ESD knife, according to one embodiment of the present disclosure.

FIGS. 6A-6B provide perspective views of a medical device cleaning tool and an ESD knife, according to one embodiment of the present disclosure.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to medical tools or accessories designed to remove debris from a fluid delivery lumen of an ESD knife, it should be appreciated that such tools/accessories may be used to clean a variety of medical (and non-medical) devices.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

Figure 1A:
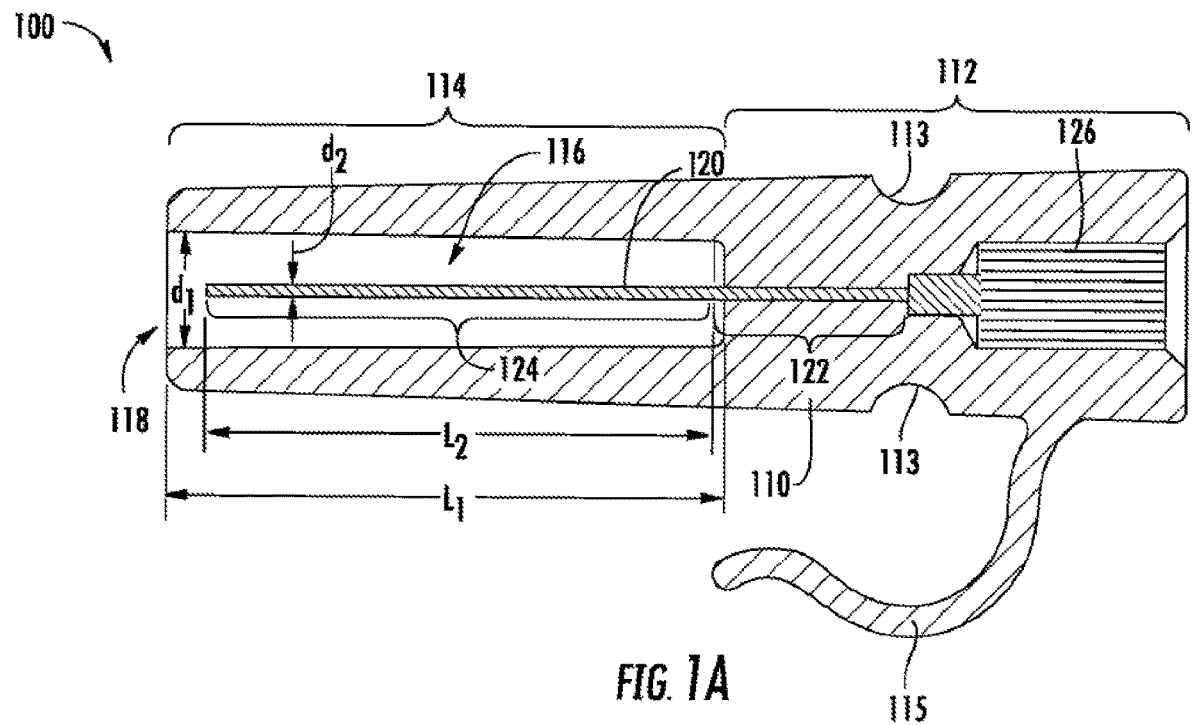
FIGS. 1A-1B provide perspective views of a medical device cleaning tool, according to one embodiment of the present disclosure.
Figure 1B:
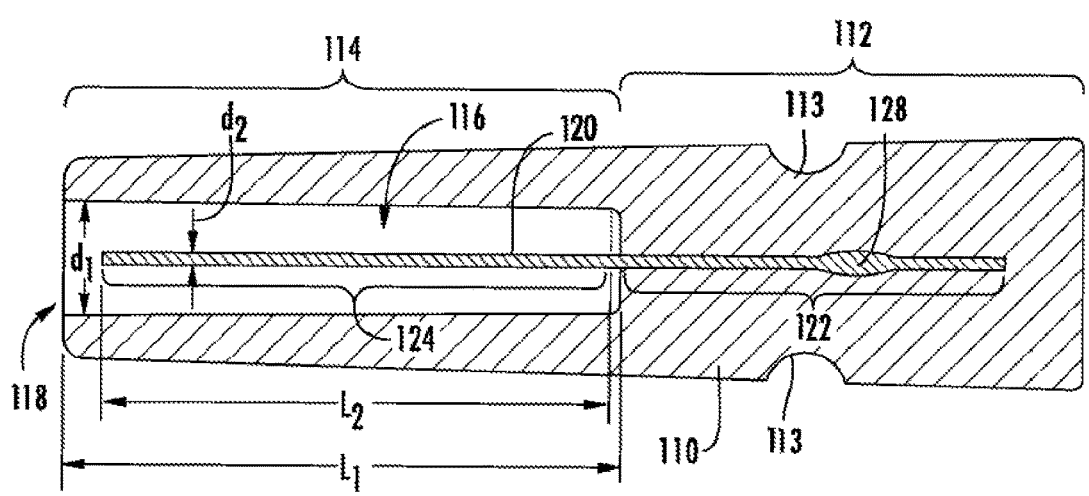
Figure 5A:
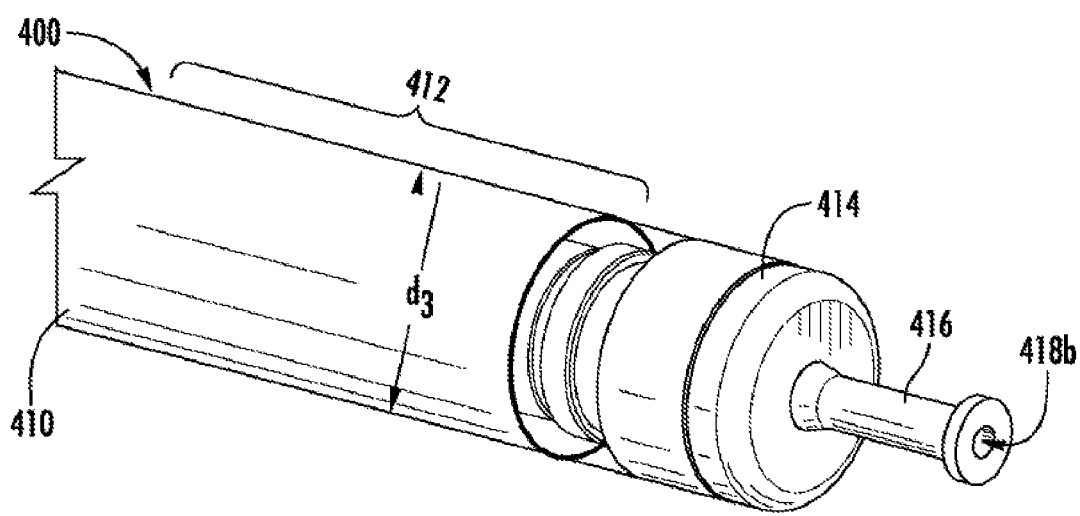

Referring to FIGS. 1A-1B, in one embodiment, a medical device (e.g., ESD knife, etc.) cleaning tool 100 of the present disclosure may include a housing 110 comprising a first (e.g., proximal) portion 112 and a second (e.g., distal) portion 114. In various embodiments, an outer surface of the housing 110 may include a decreasing diameter (e.g., taper) from the first to second portion. A chamber 116, including a distal opening 118, may be formed within the second portion 114 of the housing 110. In various embodiments, the chamber 116 may be substantially centered within the second portion 114 of the housing 110. The chamber 116 may include a substantially constant inner dimension $d_1$ and a length $L_1$ configured to receive a corresponding outer dimension $d_3$ of a distal portion of an ESD knife 400, including cutting element 416 (FIGS. 5A-5B).

Figure 6B:
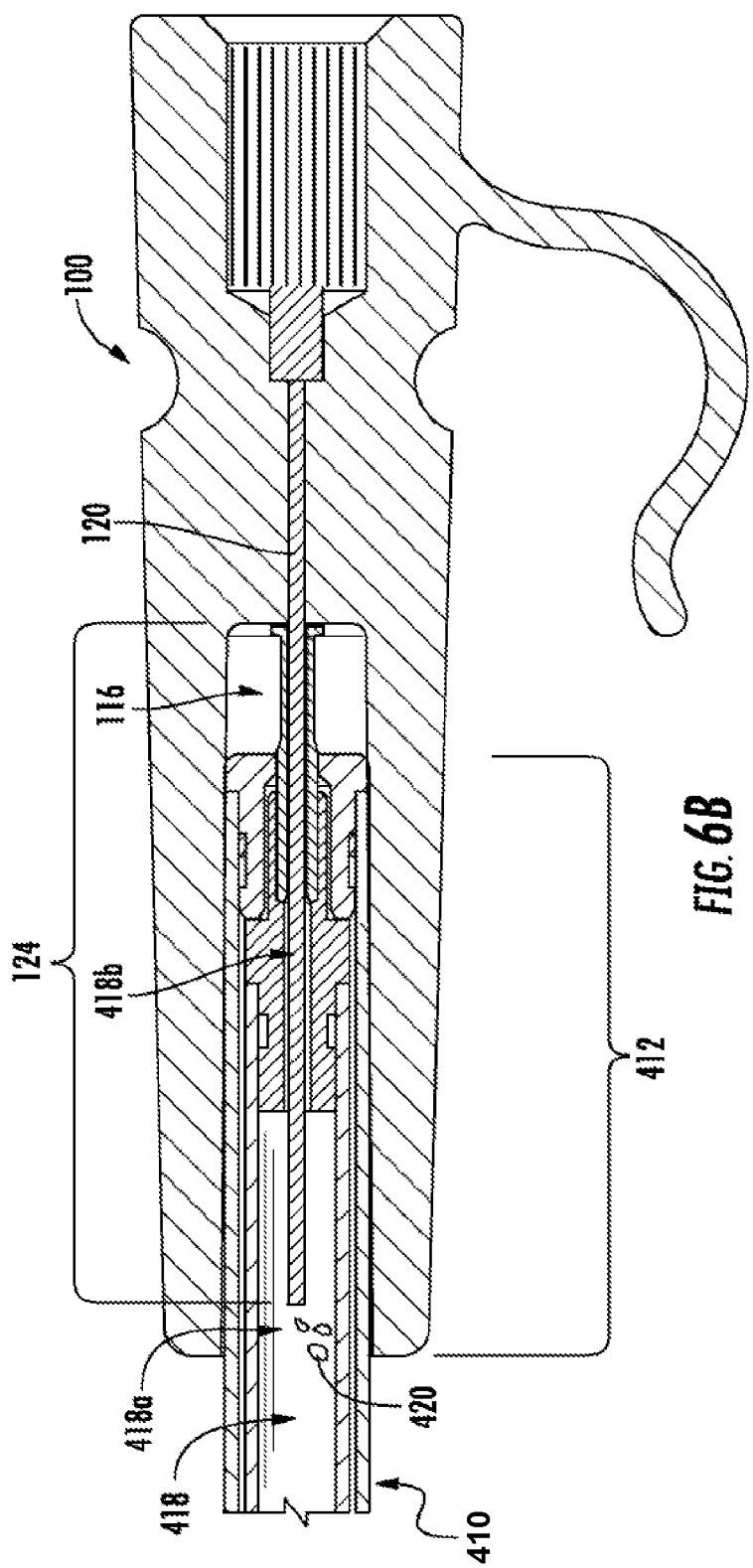

An elongate member 120 (e.g., shaft, rod, pin, post, etc.) may be disposed within the housing 110 such that a first (e.g., proximal) portion 122 of the elongate member 120 is secured (e.g., embedded, locked, immovably disposed, etc.) within the first portion 112 of the housing 110 and a second (e.g., distal) portion 124 of the elongate member 120 extends into the chamber 116. In various embodiments, the second portion 124 of the elongate member 120 may be substantially centered within the chamber 116. The second portion 124 of the elongate member 120 may include a length $L_2$ (e.g., approximately 9.0-11.0 mm) less than the length $L_1$ of the chamber 116 such that the second portion 124 does not extend beyond the opening 118 of the chamber 116 (e.g., the second portion 124 is housed entirely within the chamber 116). The second portion 124 of the elongate member 120 may include a substantially constant outer dimension $d_2$ (e.g., approximately 0.30 mm) configured to extend into (e.g., be received within) a fluid delivery lumen 418 of the ESD knife 400, including cutting element 416 (FIGS. 6A-6B). In various embodiments, an anchoring element may be attached to (e.g., using a suitable adhesive, glue, resin, solder, etc.) or integrally formed with (e.g., over-molded, co-molded, etc.) the first portion 122 of the elongate member 120 to further secure the elongate member 120 within the housing 110. By way of non-limiting example, the anchoring element may include an enlarged end section 126 (FIG. 1A) or a deformed/flattened portion 128 (FIG. 1B) embedded within the first portion 112 of the housing 110.

In various embodiments, a clip attachment 115 (e.g., clip, clasp, flexible arm, etc.) may be attached to or integrally formed with an outer surface of the first portion 112 of the housing 110. The clip attachment 115 (FIG. 1A) may be configured to removably secure or fasten the medical device cleaning tool 100 to a variety of surfaces within a medical suite to provide ready access to a medical professional and/or prevent loss or misplacement during a medical procedure. In addition, or alternatively, the outer surface of the first portion 112 of the housing 110 may include one or more surface features 113 (e.g., recessed portions, dimples, grooves, stippling patterns, etc.) to provide a medical professional with improved grip and/or ergonomics when cleaning a medical device.

Figure 2A:
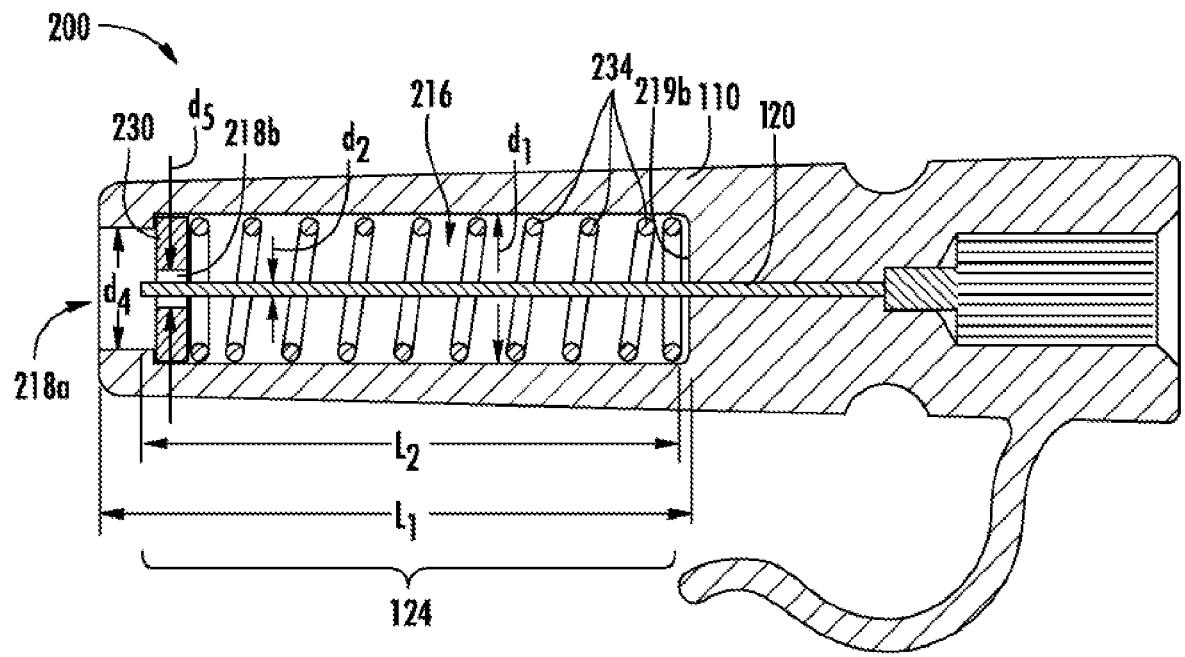
FIGS. 2A-2B provide perspective views of a medical device cleaning tool, according to one embodiment of the present disclosure.
Figure 2B:
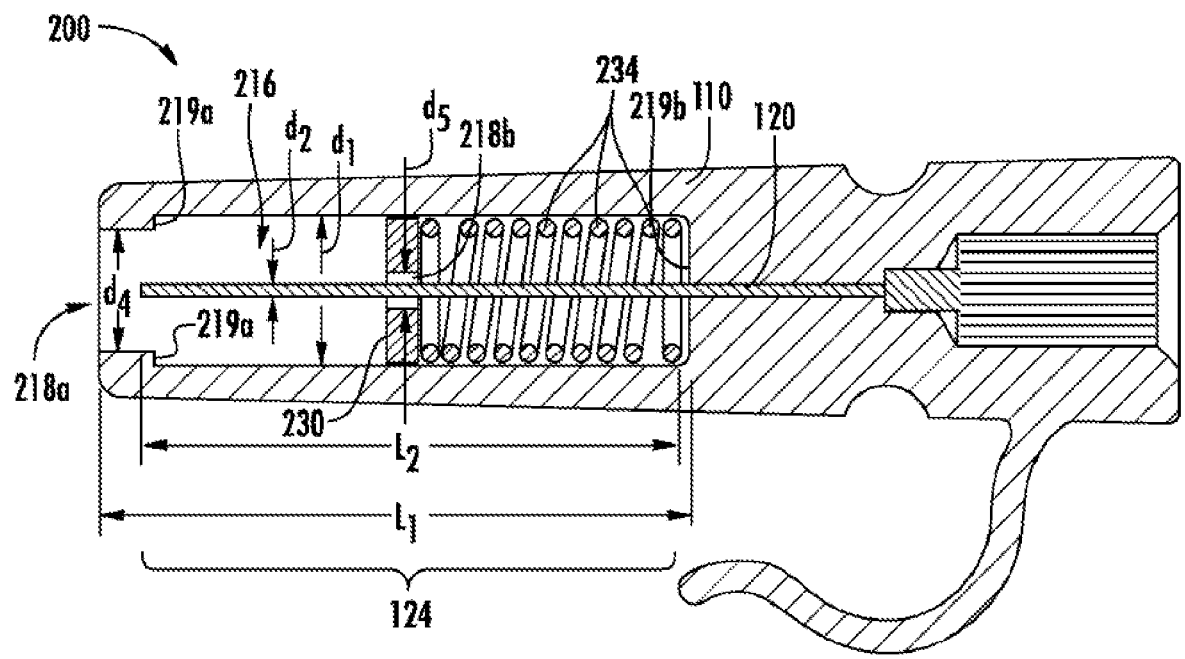

Referring to FIGS. 2A-2B, in one embodiment, a medical device cleaning tool 200 of the present disclosure may include a housing 110 and elongate member 120 comprising the same (or similar) elements as outlined in FIGS. 1A-1B, and further including a chamber 216 with a length $L_1$ and an opening 218a with a substantially constant inner dimension $d_4$ less than an inner dimension $d_1$ of the remaining portion of the chamber 216. As above, the inner dimensions $d_1$ and $d_4$ and length $L_1$ of the chamber 216 may be configured to receive an outer dimension $d_3$ of a distal portion of an ESD knife 400, including cutting element 416 (FIGS. 5A-5B). In various embodiments, the opening 218a may be defined by a thicker wall portion (e.g., projection, surface feature, etc.) that extends into the chamber to define a first substantially planar surface 219a within the chamber 216. In various embodiments, the opposite (e.g., proximal) end of the chamber 216 may define a second substantially planer surface 219b. A plate 230 may be movably/slidably disposed within the chamber 216 proximal to the planar surface 219a. The plate 230 may define an opening 218b with an inner dimension $d_5$ configured to receive the corresponding outer dimension $d_2$ of the second portion 124 of the elongate member 120. A spring 234 (e.g., a helical spring) may be disposed within the chamber 216 around the second portion 124 of the elongate member 120 and proximal to the plate 230 such that a distal end of the spring 234 contacts the first planer surface 219a and a proximal end of the spring 234 contacts the second planar surface 219b. In various embodiments, the plate 230 may move (e.g., slide, etc.) along/over the second portion 124 of the elongate member 120 from a first axial to a variety of second axial positions within the chamber 216. For example, referring to FIG. 2A, in a first axial position the plate 230 may be in contact with or adjacent to the first planar surface 219a and the spring 234 may be substantially relaxed (e.g., uncompressed, extended, etc.) within the chamber 216, thereby maintaining the second portion 124 of elongate member 120 in a non-exposed (e.g., shielded) configuration within the chamber 216. Referring to FIG. 2B, in a second axial position the plate 230 may move toward the second planar surface 219b and the spring 234 may be substantially compressed within the chamber 216, thereby exposing all or part of the second portion 124 of the elongate member 120 within the chamber 216. In various embodiments, the plate 230 may move from the first axial position to a second axial position when a distal end of an ESD knife is inserted into the chamber. In various additional embodiments, the plate may return to the first axial position from a second axial position when the ESD knife is removed from within the chamber 216. In various embodiments, in addition to shielding and/or exposing the second portion 124 of the elongate member 120 within the chamber 216, the plate 230 may support the elongate member 120 to prevent or minimize bending or kinking of the elongate member, e.g., when a distal portion of an ESD knife is inserted into the chamber 216.

Figure 3A:
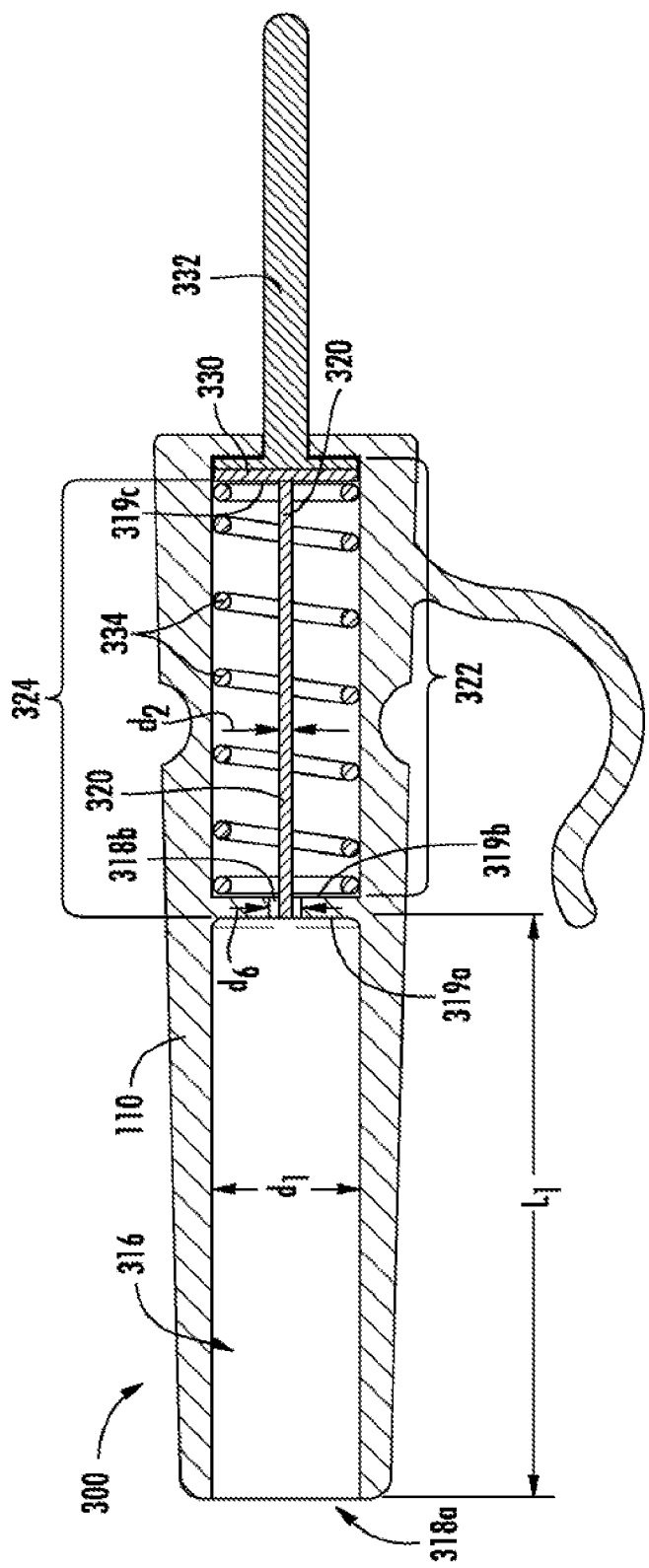
FIGS. 3A-3B provide perspective views of a medical device cleaning tool, according to one embodiment of the present disclosure.
Figure 3B:
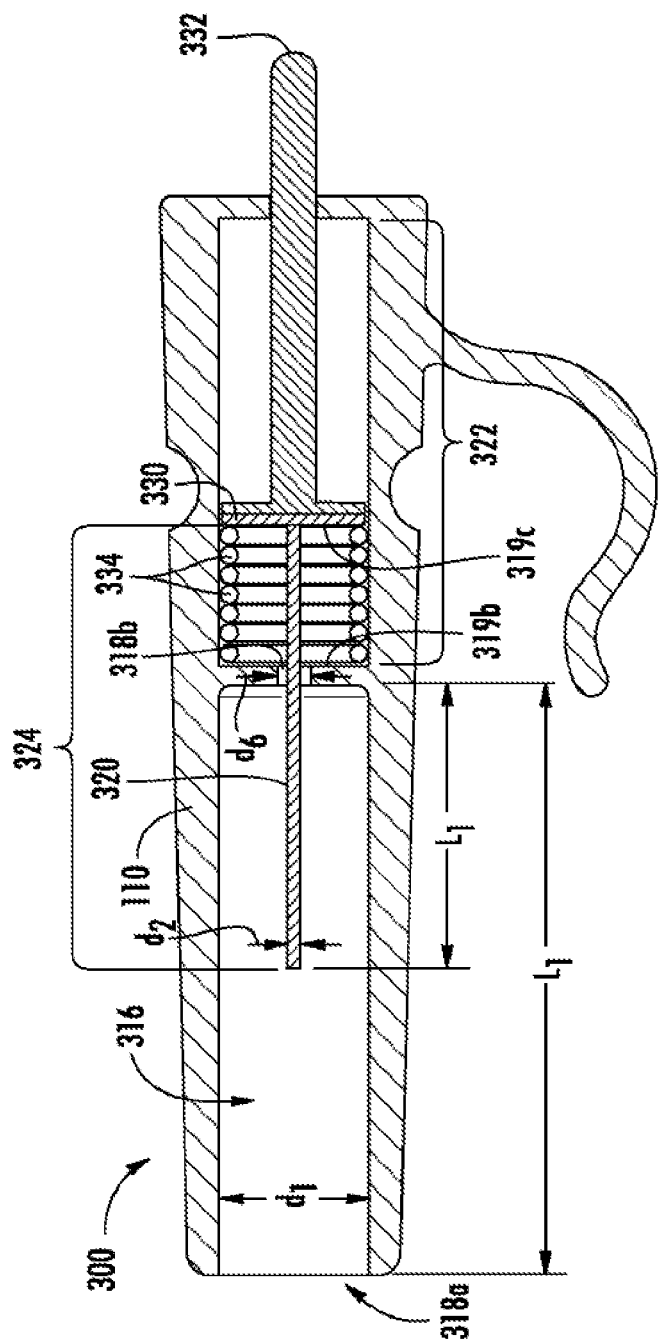

Referring to FIGS. 3A-3B, in one embodiment, a medical device cleaning tool 300 of the present disclosure may include a housing 110 comprising the same (or similar) elements as outlined in FIGS. 1A-1B, and further including a chamber 316 with an opening 318a, an inner dimension $d_1$ and a length $L_1$ configured to receive a corresponding outer dimension $d_3$ of a distal portion of an ESD knife 400, including cutting element 416 (FIGS. 5A-5B). A proximal portion of the chamber 316 may include a thicker wall portion (e.g., flange, projection, surface feature, etc.) that extends into the chamber 316 to define an opening 318b with an inner dimension $d_6$ configured to receive the corresponding outer dimension $d_2$ of an elongate member 320 (discussed below). In various embodiments, the thicker wall portion may define a first substantially planar surface 319a and a second substantially planar surface 319b within the chamber 316. An elongate member 320 may be movably/slidably disposed within the housing 110. A plate 330 may be attached to or integrally formed with a proximal end of the elongate member 320 and proximal to the second planar surface 319b. In various embodiments, the plate may define a third substantially planar surface 319c. A plunger 332 may extend through an opening (not shown) formed within a proximal end of the housing such that a distal end of the plunger is attached to or otherwise contacts a proximal end of the plate 330. A spring 334 may be disposed within the chamber 316 around a first portion 322 of the elongate member 320 and proximal to the second planar surface 319b of the thicker wall portion such that a distal end of the spring 334 contacts the second planar surface 319b and a proximal end of the spring contacts the third planar surface 319c of the plate 330. In various embodiments, the plunger may move between a first position (e.g., non-depressed) to a second position (e.g., depressed) by applying force to the proximal end of the plunger to distally advance and/or proximally retract the elongate member 320 to a variety of axial positions within the chamber 316. For example, referring to FIG. 3A, with the plunger 332 in the first position, the distal end of the elongate member 320 may extend into the opening 318b and the spring 334 may be substantially relaxed (e.g., uncompressed, extended, etc.) between the second and third planar surfaces 319b, 319c, thereby maintaining the second portion 324 of elongate member 320 in a non-exposed (e.g., non-extended, shielded, etc.) configuration within the chamber 316 (e.g., the second portion 324 of the elongate member does not extend distally beyond the opening 318b of the surface feature into the portion of the chamber 316 with the inner dimension $d_1$). Referring to FIG. 3B, with the plunger 332 in the second position, the third planar surface 319c of the plate 330 may move toward the second planar surface 319b and the spring 334 may be substantially compressed therebetween to distally advance (e.g., extend, etc.) the second portion 324 of the elongate member 320 through the opening 318b and into the portion of the chamber 316 with an inner dimension $d_1$. In various embodiments, the opening 318b may support the elongate member 320 to prevent or minimize bending or kinking of the elongate member, e.g., when a distal portion of an ESD knife is inserted into the chamber 316.

In various embodiments, a distal portion of an ESD knife 400 may be inserted into the chamber 316 such that a distal end of the ESD knife, including the cutting element 416 is in contact with or adjacent to the first planar surface 319a and the fluid delivery lumen 318 substantially aligns with the opening 318b. The plunger 332 may then be depressed to distally advance the second portion 324 of the elongate member 320 into the fluid delivery lumen 318 of the ESD knife (discussed below).

Figure 4A:
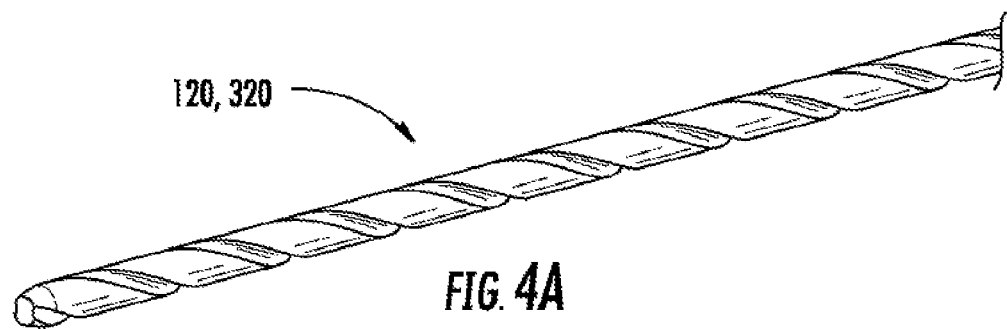
FIGS. 4A-4B provide perspective views of an elongate member of a medical device cleaning tool, according to one embodiment of the present disclosure.
Figure 4B:
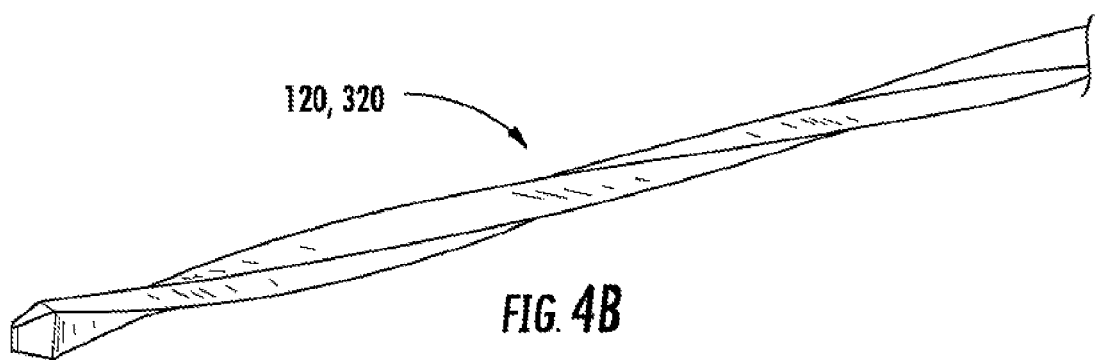

Although the elongate members 120, 320 of the medical device cleaning tools 100, 200, 300 of the present disclosure are depicted as including a substantially cylindrical outer dimension along a full length of the respective first and second portions, referring to FIGS. 4A-4B, in various embodiments the elongate members may include a variety of non-cylindrical outer dimensions. By way of non-limiting example, a helical groove may extend along all or a portion of the elongate member (FIG. 4A). In addition, or alternatively, as shown in FIG. 4B, all or a portion of the elongate member may include a helical twist, e.g., with a solid flattened profile. In various additional embodiments, the elongate member may include a variety of additional surface features (e.g., bumps, burrs, filaments, brushes, recessed portions, etc.) to break-up and/or remove debris from within the fluid delivery lumen of an ESD knife. In various additional embodiments, a channel or lumen (not shown) may extend through all or a portion of the elongate member 120, 320.

Referring to FIGS. 5A-5B, in one embodiment, an ESD knife 400 of the present disclosure may include a shaft 410 with a distal portion 412 that includes an outer dimension $d_3$, an insulated distal tip 414 and a cutting element 416. A fluid delivery lumen 418 (e.g., injection lumen, injection port, etc.) may extend through a full length of the shaft 410 and the cutting element 416. In various embodiments, the fluid delivery lumen 418 may include a main lumen 418a extending through the full length of shaft 410 and an injection lumen 418b extending through the full length of the cutting element 416, the main lumen 418a and the injection lumen 418b co-extensive with each other. The injection lumen 418b may include a length $L_3$ that is less than the length $L_2$ of the second portion 124, 324 of the elongate member 120, 320. In addition, the main lumen 418a may include an inner dimension $d_7$ and the injection lumen 418b may include an inner dimension $d_8$. The inner dimension $d_8$ of the injection lumen 418b may be less than the inner dimension $d_7$ of the main lumen 418a but greater than the outer dimension $d_2$ of the elongate member, e.g., such that the second portion 124, 324 of the elongate members 120, 320 may be received within and extend through the injection lumen 418b and into the main lumen 418a of the shaft 410.

Referring to FIGS. 6A-6B, in use and by way of example, a medical professional may break-up and/or remove debris 420 accumulated within the fluid delivery lumen 418 of an ESD knife 400 by inserting a distal portion 412 of the ESD knife 400 into the chamber 116 of a medical device cleaning tool 100 such that the second portion 124 of the elongate member 120 extends into through the injection lumen 418b and into the main lumen 418a. In this example, cutting element 416 may be positioned in an extended position (as shown) or may be positioned in a retracted position (not shown) when the distal portion 412 of the ESD knife 400 is inserted into the chamber 116 of the medical device cleaning tool 100. The medical professional may then move the medical device cleaning tool 100 back-and-forth along the distal portion 412 of the ESD knife 400, with or without a twisting motion, as necessary to break-up the debris 420 accumulated in the injection lumen 418b and/or main lumen 418a. In various embodiments, the larger inner dimension $d_7$ of the main lumen 418a as compared to the inner dimension $d_8$ of the injection lumen 418b may allow debris 420 accumulated within the injection lumen 418b to fall into the main lumen 418a, thereby restoring adequate fluid flow through the injection lumen. In addition, or alternatively, debris 420 accumulated within the main lumen 418a and/or injection lumen 418b may be removed or expelled from within shaft 410 upon removal of the distal portion 412 of the ESD knife 400 from within the chamber 116 of the medical device cleaning tool 100. For example, in embodiments of the present disclosure in which the second portion 124 of the elongate member 120 includes a surface feature (e.g., helical groove or helical twist), debris may accumulate within such surface feature(s).

Although FIGS. 6A-6B depict an embodiment of the present disclosure in which debris is removed from the injection lumen 418b of an ESD knife 400 using a medical device cleaning tool 100 of the present disclosure, in various embodiments any of the medical device cleaning tools 200, 300 disclosed herein may be used to remove such debris as discussed above. For example, a distal portion 412 of the ESD knife 400 may be inserted into the chamber 216 of the medical device cleaning tool 200 such that an end of the ESD knife contacts the plate 230 and moves the plate 230 proximally within the chamber 216 and the elongate member 120 extends into and through the injection lumen 418b and main lumen 418a. Similarly, a distal portion 412 of the ESD knife 400 may be inserted into the chamber 316 of the medical device cleaning tool 300 such that an end of the ESD knife contacts the first substantially planar surface 319a of the thicker wall portion. The plunger 332 may then be distally advanced and/or proximally retracted such that the elongate member 320 extends into and through the injection lumen 418b and main lumen 418a.

In various additional embodiments, in addition to removing debris from the injection lumen of an ESD knife, an inner surface of the chambers 116, 216, 316 of the medical device cleaning tools 100, 200, 300 disclosed herein may be configured to remove debris accumulated on an outer surface of a medical device. For example, one or more surface feature (e.g., coarse texture/coating, stippled pattern, checkered pattern, etc.) attached to (e.g., as a spray coating, etc.) or integrally formed with all or a portion of the inner surface of the chambers 116, 216, 316.

In various embodiments, any or all of the components of the housing 110 of the medical device cleaning tools 100, 200, 300 disclosed herein may be formed from (e.g., injection molded, co-extruded) or otherwise include a variety of rigid thermoplastic polymers that are resistant to various disinfecting or sterilizing modalities (e.g., chemicals, radiation, U.V. light), including, for example, polycarbonate, ABS, nylon, glass-reinforced nylon, acetal acrylic, PEET, PEEK, Pebax, polypropylene and the like.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device cleaning tool, comprising:
   a housing comprising a first portion and a second portion, wherein at least the second portion of the housing is rigid;
   a chamber formed within the second portion of the housing, the chamber defining an opening at a distal end of the housing; and
   an elongate member disposed within the housing, wherein a first portion of the elongate member is secured within the first portion of the housing and a second portion of the elongate member extends into the chamber, and wherein the first portion of the elongate member includes an anchoring element secured within the first portion of the housing.

2. The medical device cleaning tool of claim 1, wherein the second portion of the elongate member includes a length that is less than a length of the chamber.

3. The medical device cleaning tool of claim 2, wherein the length of the second portion of the elongate member is 9 mm to 11 mm.

4. The medical device cleaning tool of claim 1, wherein the anchoring element includes an enlarged end section embedded within the first portion of the housing.

5. The medical device cleaning tool of claim 1, wherein the anchoring element includes a deformed or flattened portion embedded within the first portion of the housing.

6. The medical device cleaning tool of claim 1, wherein the chamber includes a constant inner diameter.

7. The medical device cleaning tool of claim 1, wherein the second portion of the elongate member includes a helical groove or a helical twist.

8. The medical device cleaning tool of claim 1, wherein the opening of the chamber is defined by a thicker wall portion that extends into the chamber.

9. The medical device cleaning tool of claim 8, further comprising:
a plate disposed within the chamber, the plate defining an opening configured to receive the second portion of the elongate member; and
a spring disposed within the chamber and around the elongate member proximal to the plate.

10. The medical device cleaning tool of claim 1, further comprising a clip on an outer surface of the first portion of the housing.

11. A medical device cleaning tool, comprising:
a housing comprising a first portion and a second portion, wherein the housing includes a longitudinal axis extending longitudinally from an outer end of the first portion to an outer end of the second portion, and wherein the housing includes a decreasing diameter taper from the first portion of the housing to the second portion of the housing;
a chamber formed within the second portion of the housing, wherein the chamber extends along the longitudinal axis of the second portion of the housing and defines an opening at a distal end of the housing; and
an elongate member secured within the housing.

12. The medical device cleaning tool of claim 11, wherein an outer surface of the housing includes a decreasing diameter taper from the first portion to the second portion, and wherein at least the second portion of the housing is rigid.

13. The medical device cleaning tool of claim 12, wherein a first portion of the elongate member is secured within the first portion of the housing and a second portion of the elongate member extends into the chamber.

14. The medical device cleaning tool of claim 13, wherein the first portion of the elongate member includes an anchoring element secured within the first portion of the housing.

15. The medical device cleaning tool of claim 14, wherein the anchoring element includes an enlarged end section embedded within the first portion of the housing.

16. The medical device cleaning tool of claim 14, wherein the anchoring element includes a deformed or flattened portion embedded within the first portion of the housing.

17. The medical device cleaning tool of claim 14, wherein the second portion of the elongate member includes a length that is less than a length of the chamber.

18. A medical device cleaning tool, comprising:
a housing comprising a first portion and a second portion;
a chamber formed within the second portion of the housing, the chamber defining an opening at a distal end of the housing; and
an elongate member fixed within the housing, wherein the elongate member includes an enlarged end section within the first portion of the housing and a portion that extends into the chamber,
wherein at least the second portion of the housing is rigid,
wherein the opening and chamber of the housing include an inner dimension configured to receive a corresponding outer dimension of a medical device, and
wherein the portion of the elongate member that extends into the chamber includes an outer dimension configured to extend into a fluid delivery lumen of the medical device.

19. The medical device cleaning tool of claim 18, wherein the portion of the elongate member includes a length that is less than a length of the chamber, wherein the housing includes a longitudinal axis extending longitudinally from an outer end of the first portion to an outer end of the second portion, and wherein the chamber extends along the longitudinal axis of the second portion of the housing.

20. The medical device cleaning tool of claim 18, further comprising a clip on an outer surface of the first portion of the housing.

* * * * *